United States Patent [19]

Beattie et al.

[11] Patent Number: 5,116,753
[45] Date of Patent: May 26, 1992

[54] MAINTENANCE OF PANCREATIC ISLETS

[75] Inventors: Gillian M. Beattie, Poway; Douglas A. Lappi, Del Mar; J. Andrew Baird, San Diego; Alberto Hayek, La Jolla, all of Calif.

[73] Assignees: The Salk Institute for Biological Studies, La Jolla; The Whittier Institute for Diabetes & Endocrinology, San Diego, both of Calif.

[21] Appl. No.: 737,758

[22] Filed: Jul. 30, 1991

[51] Int. Cl.$^5$ .......................... C12N 5/06; C12N 5/08
[52] U.S. Cl. .......................... 435/240.2; 435/240.21; 435/240.3; 435/240.31
[58] Field of Search ............ 435/240.2, 240.21, 240.3, 435/240.31

[56] References Cited
PUBLICATIONS

Beattie et al., J. Clin. Endocrinol Metab 73(1): 93-98 (1991).

Beattie et al., Diabetes 39(8): 1002-1005 (1990).

Primary Examiner—Douglas W. Robinson
Assistant Examiner—Jean C. Witz
Attorney, Agent, or Firm—Fitch, Even, Tabin & Flannery

[57] ABSTRACT

The addition of basic FGF-saporin mitotoxins selectively elminates fibroblastoids from human islets in culture and increases the ability of such islets to release insulin under basal and stimulated conditions. When such islets are attached to an extracellular matrix, in particular BCEM, the proliferation of islet cells is favored, and the ability of islets cultured in such manner to release insulin is further increased. Moreover, supplementation of the culture media with high glucose or insulin further improves the functioning of the human islets, resulting in augmented insulin release. Combinations of such procedures offer a novel approach towards the establishment of viable human islet cell monolayers for clinical and laboratory research.

13 Claims, No Drawings

MAINTENANCE OF PANCREATIC ISLETS

This invention was made with Government support under Grant Nos. DK-18811 and DK-39087, awarded by the NIDDKD, one institute of the National Institutes of Health. The Government has certain rights in this invention.

This invention generally relates to the maintenance of pancreatic islets in culture. More specifically, it relates to the use of a fibroblast growth factor ligand conjugated to a cytotoxic agent in a manner to inhibit the proliferation of undesired cells and thereby enhance islet monolayer growth of mammalian, particularly human, islets for use in laboratory research and for potential clinical use.

BACKGROUND OF THE INVENTION

Insulin is produced by the islets of Langerhans within the pancreas, and the specific hormone-producing cells which make insulin are called the beta cells. Insulin helps most cells of the body take up biological fuels, including the sugar glucose. As pancreatic beta cells are killed during the onset of juvenile diabetes, the pancreas stops producing this hormone, and glucose accumulates in the blood, giving rise to abnormally high glucose levels that are a sign of diabetes. The body then becomes dehydrated as the kidneys overwork to filter the excess glucose into the urine. Meanwhile other body cells essentially starve in a sea of plenty and begin to uncontrollably break down their stores of fat and protein to provide more fuel. If such breakdown of fat continues unchecked, acidic by-products, i.e. ketones, build up which, combined with dehydration, can induce coma and death.

Insulin injections are generally able to halt this lethal sequence and prevent it from recurring, but they cannot mimic the normal pattern of insulin release by the pancreas. Moreover, they cannot normalize metabolic functioning well enough to prevent the long term complications of diabetes which are generally believed to be caused or exacerbated by chronically elevated blood glucose levels.

The beta cells of the pancreas are destroyed in various ways, and one is believed to be via an autoimmune process. Although animal insulin and the more modern recombinant human form thereof offer temporary treatment in response to the destruction of the beta cells and thus survival for millions of diabetics, neither offers a cure because injections or other administration of insulin must be taken once or more a day for life. In addition, many diabetics eventually suffer from devastating complications, including heart disease, blindness and kidney failure.

Advances in automated methods to isolate human pancreatic islets have increased the availability of preparations rich in endocrine tissue for clinical and laboratory research directed to insulin production and related aspects of diabetes. These efforts have led to the first successful, albeit transitory, transplantation of islets into a Type 1 diabetic patient and to the establishment of an islet distribution center which supplies human islets for research to investigators in the United States.

Pancreatic islets do not grow readily in primary cultures; however, these endocrine cells have been grown with difficulty as monolayers. The difficulty of long-term culture has not only hindered the laboratory research for such islets, but it has also hindered attempts to carry out physiological and even clinical studies with such islets. It had been previously shown that it is possible to eliminate inherently contaminating fibroblasts in monolayer cultures of neonatal pancreatic islets by keeping the islets free-floating in petri dishes for 5 days before the transfer of the islets to coated dishes. Because this approach was not always feasible and because the survival of adult islets was curtailed under these conditions, fibroblast contamination has remained a problem.

The addition of various inhibitors of fibroblast proliferation has not yet solved this problem. More specifically, to rid islet cultures of fibroblasts to the culture medium, attempts were previously made to add the following compounds as inhibitors of fibroblast growth: thimerosal (Kaiser, N. et al., *Endocrinology*, 123, 834–840, 1988), iodoacetic acid (Shimuzu, S. et al., *Endocrinol. Jpn.*, 31, 253–261, 1984) and 2-deoxyglucose (Yoshida, K., et al., *B.B.R.C.*, 108, 279–285, 1982). However, these efforts were met with only limited success, and generally investigators were faced with the decantation of pancreatic cell suspensions into new dishes after each few hours of culture, followed by culture in a medium which is free of cysteine and serum, Hayek, A. et al., *In Vitro*, 25, 146–150 (1989). Therefore, improved ways of maintaining pancreatic islets in culture continue to be avidly sought.

SUMMARY OF THE INVENTION

It has been found that the use of biocompatible matrices for growth together with the selective elimination of proliferating fibroblasts by adding specific mitotoxins clearly increase the ability of human islets in short-term culture to survive and release insulin under basal and stimulated conditions. The greatest improvement in islet cell function in either static or stimulated situations is obtained when a bovine corneal endothelial cell (BCEM) is used as an extracellular matrix, when the media is supplemented with a relatively high concentration of glucose or insulin, and when the cultures are exposed to a basic FGF-saporin mitotoxin.

DETAILED DESCRIPTION OF PREFERRED EMBODIMENTS

There have been a number of obstacles to the induction and maintenance of pancreatic islet monolayers; one obstacle has been contamination by fibroblasts, the proliferation of which inhibits the survival of the endocrine cells and thus greatly reduces the possibility of maintaining long-term cultures. It has now been surprisingly found that the administration of a particular mitotoxin which is a chemical conjugate of basic FGF (a molecule which promotes mitosis) and a toxin, preferably a ribosome-inactivating protein such as saporin, is very effective in greatly enhancing the likelihood of long-term maintenance of pancreatic islets, particularly pancreatic islet monolayers, because it is able to selectively destroy fibroblast cells without any measurable harm to the important cells of the islets.

Basic fibroblast growth factor (bFGF) is a protein which has a molecular weight of greater than about 16 kD, is acid- and temperature-sensitive and has a high isoelectric point. bFGF exhibits mitogenic effects which have stimulated considerable interest in its use as a potential therapeutic agent for wound healing, nerve regeneration and cartilage repair, for example. The amino acid sequence of mammalian bFGF, in the form of the structure of the 146-amino acid bovine molecule obtained from bovine pituitary tissue, was first reported in Esch et al, *P.N.A.S.*, 82, 6507 (1985), and also set forth in U.S. Pat. No. 4,956,455, issued Sep. 11, 1990, the disclosure of which is incorporated herein by reference. cDNA encoding bovine bFGF has been cloned and sequenced and predicts the existence of a protein identical to bovine bFGF as found by protein sequencing, see Abraham et al., *Science*, 233, 545–548 (1986). The protein sequences of human bFGF, see Abraham et al., *EMBO J.*, 5, 2523 (1986), and Abraham et al., *Quant. Biol.*, 51, 657–668 (1986), and rat bFGF, see Shimasaki et al., *B.B.R.C.* (1988) and Kurokawa et al., *Nucleic Acids Res.*, 16, 5201 (1988) have also been deduced as highly homologous proteins.

Basic FGF is commercially available, for example, from Amgen (Thousand Oaks, CA) and from Amersham International. It can also be obtained from a variety of tissues of mammals via methods of purification using reverse-phase high performance liquid chromatography (RPHPLC) and/or heparin-Sepharose affinity chromatography. In addition, bFGF can be synthesized using recombinant methods. Expression of a recombinant protein in yeast and *E. coli* is described in Barr et al., *J. Biol. Chem.*, 263, 16471–16478 (1988) and in U.S. Pat. No. 4,956,455. The term "bFGF" should be generally understood to refer to proteins or polypeptides having substantially the same amino acid sequence and mitogenic activity as that of bovine bFGF or human bFGF.

Cells that respond to basic FGF have now been shown to possess specific receptors on the cell surface membranes. In addition to basic FGF, there are known to be a number of other proteins, e.g., acidic FGF, exhibiting basic FGF mitogenic activity mediated through binding to an FGF receptor. The term FGF is generally used to refer both to proteins having amino acid sequences found in a mammalian host, as well as modified sequences having amino acid substitutions, deletions, insertions or additions which still express mitogenic activity, mediated through binding to an FGF receptor. As used herein, the term "FGF receptor" is used to refer to receptors, particularly the high-affinity receptors, which are able to bind basic FGF and transport it into the cell. It was surprisingly found that pancreatic islet cells in culture do not express the high-affinity FGF receptor.

The receptor proteins appear to be single chain polypeptides with molecular weights ranging from 110 to 150 kD, depending on cell type. These receptor proteins bind basic FGF with high affinity ($Kd = 10$–$80$ pM), and receptor numbers often range from 2000 to 80,000 per cell. Such receptors have been purified from chicken embryo and from rat brain, using a combination of lectin and ligand affinity chromatography and are associated with tyrosine kinase activity, see Imamura et al., *B.B.R.C.* 155, 583–590 (1989); Huang and Huang, *J. Biol. Chem.*, 261, 9568–9571 (1986); and Moscatelli, *J. Cell. Physiol.*, 131, 123–130 (1987). On baby hamster kidney cells (BHK), two basic FGF receptors with estimated molecular weights of 110 and 130 kD have been reported in Neufeld et al., *J. Biol. Chem.*, 260, 13860–13868 (1985) and Neufeld et al., *J Biol. Chem.*, 261, 5631–5637 (1986). It appears that the larger receptor protein binds bFGF preferentially and is sometimes referred to as the "high affinity" bFGF receptor. As used herein, the term "ligand reactive with the FGF receptor" refers to a polypeptide or non-peptide equivalent which is capable of binding an FGF receptor and of being transported into the cell thereby.

The feasibility of using receptor-specific ligands to transport toxins into cells has recently been demonstrated. The strategy, originally applied in immunotherapy by conjugating toxins to monoclonal antibodies (see Blakey et al., *Cancer Research*, 48, 7072–7078 (1988)), has recently been pursued by coupling toxins with classic endocrine hormones, such as CRF and TRF, with cytokines, such as EGF and TGFα, and with lymphokines, such as interleukin-2. U.S. Pat. No. 4,468,382 to Bacha et al. shows cytotoxic conjugates wherein the hormone TRH is linked to the toxin CRM 45 by a disulfide bond between linkers covalently attached to a histidine residue and the toxin to produce a toxic hybrid protein alleged to be useful in the treatment of certain tumors.

By coupling a ligand, such as basic FGF, to Saporin-6 (SAP), a ribosome-inactivating protein (RIP) isolated from the seeds of the plant *Saponaria officinalis*, there is produced a powerful mitotoxin, i.e., a cytotoxic molecule targeted to specific cells by a mitogen, which is termed FGF-SAP. Certain conjugates like these are disclosed in International Application published Nov. 1, 1990 as WO 90/12597, in the names of D.A. Lappi and A. Baird, claiming priority from U.S. Application Ser. No. 344,109 (27 Apr. 1989), the disclosure of which is incorporated herein by reference. They are also described in Lappi, D. et al., *B.B.R.C.*, 160, 917 (1989). It has now been discovered that undesirable growth of fibroblast cells in cultures of pancreatic islets can be inhibited by the administration of conjugates of an appropriate ligand, such as bFGF or its appropriate fragment or analog, and a cytotoxic agent, without harming the beta-cells of the pancreatic islets; the preferred conjugate is FGF-SAP.

Administration of a conjugate of bFGF-saporin to the medium wherein such islets are being grown upon extracellular matrices has proved effective to maintain viable, insulin-producing cultures of such islets. The conjugates should comprise a ligand, such as basic FGF or an appropriate basic FGF fragment or analog which binds to the high-affinity FGF receptor, and a cytotoxic agent, preferably a ribosome-inactivating protein (RIP), such as saporin—although other cytotoxic agents can also be advantageously used.

As used herein, the term cytotoxic agent refers to a molecule capable of inhibiting cell function. The term includes agents which are only toxic when transported into the cell and also those whose toxic effect is mediated at the cell surface. A variety of cytotoxic agents can be used, particularly those which inhibit protein synthesis. Preferably, bFGF is combined with the ribosome-inactivating protein saporin-6 (SAP), or some other appropriate SAP derivative. As earlier indicated, SAP is a potent RIP which is isolated from the seeds of the plant *Saponaria officinalis*, see Stirpe et al., *Biochem J.*, 216, 617–625 (1983). Other, appropriate cytotoxic agents include, but are not limited to, ricin, ricin A chain, gelonin, diphtheria toxin, diphtheria toxin A chain, pokeweed antiviral protein and Pseudomonas exotoxin. Alternatively, it may be feasible to use a drug as the cytotoxic agent; examples of such drugs include anthracyclines, such as the daunomycins (including daunorubicin and doxorubicin) and methotrexate and its analogs.

The ligand, which conjugated to the cytotoxic agent, is used to target the cytotoxic agent to specific cells of interest. The cytotoxic agent is attached to the ligand through a chemical bond, or alternatively, the composition is prepared as a chimera using recombinant DNA techniques. In either case, the conjugate molecule is designed and produced in such a way that the receptor binding epitope of the ligand moiety of the complex is left available for recognition by the high-affinity FGF receptor. A ligand, such as bFGF, is suitably conjugated to a protein cytotoxic agent by known chemical reactions, such as through derivatization with a reactive sulfhydryl-containing moiety, such as SPDP, or via a cross-linking agent, such as glutaraldehyde or carbodiimide. For example, the cytotoxic agent may be derivatized with a reactive sulfhydryl containing agent, such as N-succinimidyl-3(2-pyridyldithio)propionate, before bFGF is added and mixed therewith. The bFGF conjugate can be separated from the unreacted products on a suitable column. Alternatively, bFGF can be conjugated to a drug, such as 14-bromo doxorubicin through the sugar moiety, as by the cis-aconitase method, see Shen and Riser, B.B.R.C., 102, 1048 (1981). Such an FGF-cytotoxic agent conjugate can be purified on a column containing immobilized heparin--for example, columns of heparin Sepharose or heparin-agarose. The bound conjugate can be eluted with a salt gradient, such as NaCl, and elutes between 1 and 3 M NaCl.

Alternatively, chimeric FGF-conjugates can be prepared by recombinant methods. Such methods as applied to conjugates of IL-2 or TGFo are described in Chaudhary et al., P.N.A.S., 84, 4538-4542 (1987) and in Lorberman-Galski et al., P.N.A.S., 85, 1922-1926 (1988). See also Maniatis et al., *Molecular Cloning: A Laboratory Manual*, Cold Spring Harbor Laboratory (1982).

Islets for use in experiments to test the efficacy of the invention are isolated from highly inbred Lewis rats originally obtained through the National Institutes of Health Grantee Reimbursement Program from the Charles River Breeding Laboratories (Charles River, MA). Male rats, 150-250 g, are used as donors, and islets are isolated by the method of Lacy and Kostianovsky (Lacy PE, Kostianovsky M: Method for the isolation of intact islets of Langerhans from the rat pancreas, *Diabetes* 16:35-39, 1967), with collagenase B for digestion, reversibly stained with dithizone and handpicked under direct vision with a stereomicroscope.

Monolayers are fixed overnight at room temperature in 1% formalin in phosphate-buffered saline. Cells are permeabilized by incubation with 1% Nonidet P-40 in phosphate-buffered saline for 15 minutes and stained with the immunoalkaline phosphates technique with guinea pig, anti-beef insulin as the primary antibody. The slides are counterstained with hematoxylin, and Student's t tests for paired data are performed by use of the Crunch statistical package (Jandel, San Francisco, CA).

A bovine corneal endothelial cell matrix (BCEM) is prepared by lysing confluent bovine corneal endothelial cells with 1mM ammonium hydroxide for 15 minutes as generally described in the article by D. Gospodarowicz "Preparation of extracellular matrices produced by cultured bovine corneal endothelial cells and PF-HR-9 endodermal cells: their use in culture", *Cell Culture Methods for Molecular and Cell Biology*, Barnes DW, Sirbasku DA, Sato GH, Eds. New York, Liss, 1984, p. 275-95. Islet monolayer formation is initiated on BCEM-coated 24-well plates with 20 islets/well in RPM1-1640 medium containing 22.2 mM glucose and 10% fetal calf serum. At this time, saporin alone, bFGF alone or the bFGF-SAP is added. The medium is changed after 48 hours, and fresh factors are added. Islet attachment and the extent of endocrine and fibroblast proliferation are determined by visual examination with a phase-contrast microscope at 96 hours. At that time, fresh medium without the test additives is added.

At the end of 5 days, monolayers are stimulated with glucose to measure insulin release into medium in response to glucose stimulation. The cells are washed twice in Krebs-Ringer bicarbonate buffer, pH 7.4, supplemented with 2 mg/ml of bovine serum albumin, and incubated for 1 hour with low (1.6 mM) or high (16.7 mM) glucose content. Insulin release into buffer is measured by radioimmunoassay.

EXAMPLE I

In an experiment carried out using the protocol set forth hereinbefore, it was found that the addition of 10 nM FGF-SAP had no deleterious effect on the adherence of such islets to the BCEM or to the production of endocrine monolayers. The results are set forth in Table 1:

TABLE 1

Islet attachment, monolayer formation, and growth of fibroblasts after 96-hour culture in medium containing bFGF-saporin mitotoxin or one of the individual components.

| Additions to Medium | Attachment (%) | Monolayers (%) | Fibroblasts Present (%) |
|---|---|---|---|
| 10 nM FGF-saporin | 77 | 100 | 1 |
| 10 nM FGF + 10 nM saporin | 70 | 91 | 57 |
| 10 nM FGF | 61 | 94 | 57 |
| 10 nM saporin | 63 | 100 | 61 |
| 1 μM saporin | 24 | 53 | 5 |
| No additions | 73 | 100 | 69 |

NOTE:
10-20 islets/well were used for a total of at least 100 islets for each experimental observation. Islets were considered attached when manual agitation failed to displace them from the matrix. Monolayer values are given for islets that formed monolayers after 5 days in culture; "fibroblasts present" refers to fibroblast growth around individual islets.

The test results show there was virtually complete inhibition of the growth of fibroblasts around the endocrine monolayer in the mitotoxin-treated wells. There was no inhibitory effect of equimolar concentration of basic FGF, saporin, or a mixture of the two, demonstrating the specificity of the mitotoxin activity. At higher concentrations of saporin (1 μM), there was a non-specific cytotoxin effect in which endocrine and fibroblast cells were inhibited, both from adhering to the matrix and from forming monolayers.

The effect of the mitotoxin on fibroblast growth is clear, for in the untreated wells, endocrine monolayers are surrounded by fibroblasts, whereas in the treated wells, the area around the endocrine monolayer is free from non-epithelial cells. Most of the endocrine cells in the monolayer stained for insulin. Insulin release in control and in mitotoxin-treated cells was comparable after stimulation of the cells by glucose. The difference in response between basal and stimulated release was highly significant in both groups ($P<b$ 0.001). The FGF-SAP mitotoxin is specifically cytotoxic for contaminating fibroblasts and endothelial cells, has no cytotoxic effect on the β-cells of the islets, and does not impede islet response to glucose in terms of insulin release.

EXAMPLE II

Another set of experiments are carried out in which fibroblasts are selectively eliminated with a FGF-SAP mitotoxin in order to purify the endocrine cell population of cultured human islets. In these experiments, the mitotoxin is used at a concentration of 10 nM. Groups of 20 human islets are plated on BCEM-coated dishes in RPMI 1640 medium supplemented with 22.2 mM glucose and incubated for 96 hours with the mitotoxin. After 7 days, the dishes are observed for the presence of fibroblasts and subjected to functional studies to evaluate islet response to standard secretagogues as described below. Selected dishes are also assessed by immunocytochemical staining.

All incubations are carried out at 37° C. in a humidified atmosphere of 5% $CO_2$ in air. When human insulin is added to the incubation media, the FBS content is reduced to 1%. Glucose-supplemented media which is used contains 22.2 mM glucose. To prevent interference of the supplemented media with the assay conditions, particularly in the insulin-supplemented media, the monolayers are washed 3 times in a phosphate buffer and incubated in regular medium for an additional day. After this, samples of the incubation media are collected to determine the 24 hour insulin release into medium. In addition, acute insulin release is also determined in response to stimulation with Krebs Ringer buffer containing 16.7 mM glucose.

The amount of insulin released into medium from islets on the different matrices is measured daily from days 5 to 11 of culture. When the experiment is terminated, the cells are sonicated, and the extracts are used in a fluorometric DNA assay. At the end of the initial 5 days in culture, some of the islet preparations are washed twice in Kreb's Ringer bicarbonate buffer, pH 7.4, supplemented with 2 mg/ml of bovine serum albumin and incubated for 60 minutes at a glucose content of 1.6 mM. Insulin and glucagon are then measured in response to 60-minute incubations in buffer with a glucose concentration of 16.7 mM for insulin, or 10 mM for glucagon. Insulin content in the media and in acid-ethanol extracts of the islet cells is determined by a solid-phase radioimmunoassay. Glucagon content is assayed by a double antibody radioimmunoassay.

For immunohistochemical examination, monolayers are fixed overnight at room temperature in 1% formalin in PBS. Cells are permeabilized by incubation with 1% NP40 in PBS for 15 minutes and stained with the immunoalkaline phosphatase technique using guinea pig anti-insulin, rabbit anti-glucagon and rabbit anti-somatostatin antibodies.

Data are presented as a mean ± standard deviation of one experiment which is representative of at least 3 experiments using different preparations of islets. Student's t-tests for paired and unpaired data are performed using the Crunch Statistical Package.

After initial isolation of the islets, purity ranged from 70 to 95%, determined visually; islets ranged from 50 to 300 μ in diameter, with the majority measuring 50 to 100 μ. Insulin content is approximately 0.15 mU per islet, and stimulation with 16.7 mM glucose gave insulin values 3 to 5 fold over baseline.

The effect of treatment of monolayers with the FGF-SAP conjugate is striking. There is complete elimination of fibroblastoid cells in the medium containing the mitotoxin, while in the untreated dishes endocrine monolayers are surrounded by proliferating nonendocrine cells. The endocrine cells are positive for insulin, glucagon, or somatostatin when immunostained for these hormones and the non-endocrine cells are negative. In the treated dishes, on the other hand, virtually all cells remaining after the mitotoxin treatment are positive for either insulin, glucagon or somatostatin. In both treated and untreated dishes, at least 90% of the cells stain positively for insulin, while staining for other hormones, in most cases, is restricted to individual or very small cell clusters within the attached islet.

Additional testing, reported in Table 2 shows that neither glucose-stimulated insulin release nor alanine-stimulated glucagon release was impaired in the cells exposed to the mitotoxin.

TABLE 2

Insulin and glucagon release in response to acute stimulation with glucose or alanine, respectively, from cultures treated with FGF-SAP conjugate and control islets.

| Basic FGF-Saporin | 10 nM | None (control) |
|---|---|---|
| | fmoles/well/hr (Δ) | fmoles/well/hr (Δ) |
| Glucose-Stimulated Insulin-Release | 3096 ± 1128* | 2568 ± 1056* |
| Alanine-Stimulated Glucagon-Release | 1104 ± 312* | 624 ± 360* |

Each well contained 20 islets following attachment and exposure to FGF-SAP conjugate. Eight wells are used for each observation.
The Δ alanine release was lower in the control wells because the basal value (1002 ± 365 fmoles/well/hr.) was higher than that measured in the FGF-SAP treated islets (463 ± 127 fmoles/well/hr).

*$p < 0.002$ for difference between basal and stimulated values. Islets were stimulated for 60 min. with 16.7 mM glucose for insulin release and with 10 mM alanine for glucagon release.
Δ: Difference between basal and stimulated concentrations.

There was also no statistical difference between daily insulin release (42.38±3.5 pmoles in the mitotoxin-exposed dishes, as compared to 38.78±6.4 pmoles/well/24 hours in the unexposed dishes). The same was true for insulin content of islets: 37.8±5.76 pmoles per each well which was exposed to FGF-SAP, as compared to 28.98±4.68 pmoles per each well which did not contain the conjugate.

In separate experiments, the glucose-stimulated insulin release was calculated, both per μg DNA and per well, in mitotoxin-exposed and non-exposed cells. The results showed that the rate of stimulated insulin release was more efficient for those cells in which the fibroblastoid cells had been removed by the mitotoxin, and moreover, when the same data are expressed in terms of DNA content, a much more dramatic difference is apparent when the decreased non-epithelial content of the mitotoxin-treated dishes is taken into consideration.

The effect of the different matrices on the release of insulin into medium by the human islet monolayers was also measured. Only dithizone-stained islets, 20 or 30 per well, are plated on substrate-coated or 24-well polystyrene tissue culture treated plates. Substrates used to facilitate islet attachment are poly-L-lysine $M_r$ 70,000–150,000, gelatin, collagen, a solubilized basement membrane produced by mice sarcoma (Matrigel, Collaborative Research Inc., Bedford, MA) and bovine corneal endothelial cell matrix (BCEM). The results show that the 24-hour insulin release was significantly enhanced in the islets attached to BCEM, as compared to all other matrices. This level of insulin release was maintained throughout the 11 days of culture. Glucose-stimulated insulin release on day 6 of culture was also doubled in monolayers grown on BCEM, as compared to uncoated dishes (4191±136 vs. 2225±135 fmoles/well/hour; $p<0.03$). In contrast, glucose-stimulated insulin release was not as efficient when islets were grown on gelatin, poly-L-lysine, collagen or matrigel. Insulin content was also higher in islets grown on BCEM than on uncoated wells (27.24±4.2 vs. 10.08±0.72 pmoles/well, p<0.007), and insulin content of islets grown on the other matrices was similar to that on uncoated wells.

It was also found that insulin release from islets attached to BCEM was further significantly enhanced when the media was supplemented with either 22.2 mM glucose or 10 µg/ml of human insulin (p.<0.04 for 24-hour insulin release). It is generally felt that such improvement in the viability of pancreatic islets is obtained by supplementing the culture media with at least about 10 mM glucose (e.g., 11.1 millimolar) and/or at least about 5 µg/ml of human insulin, preferably recombinant human insulin.

Thus the use of biocompatible matrices in combination with the selective elimination of fibroblasts by specific mitotoxins clearly increases the health and viability of human islets, as measured by their ability to release insulin under basal and stimulated conditions in short-term culture. Moreover, the use of media supplemented with high glucose (e.g., at least about 10 millimolar) and/or insulin (e.g., at least about 5 µg/ml) is also advantageous. In general, the insulin content of islets grown on BCEM was similar to the content of freshly isolated islets, and supplementation of the media with either glucose or insulin further improved the functioning of the human islets, as demonstrated by augmented insulin release in response to challenge testing.

The efficiency with which a cytotoxin, such as saporin or a ricin A chain or a similar protein, can inhibit protein synthesis and consequently interfere with DNA synthesis is fairly widely known. Accordingly, the dosage of the conjugate that is administered will, to some extent, depend upon the particular cytotoxin chosen; however, doses of the conjugate in the concentration range of about 100 pM to about 50 mM of the conjugate are expected to be employed on a daily basis.

In summary, non-endocrine cells were effectively removed by vigorous treatment with the basic FGF-saporin conjugate. The treatment with the mitotoxin had no inhibitory effect on insulin content, chronic insulin release or on secretagogue stimulation of α- or β-cells. Traditionally, insulin release from isolated islets in culture has been expressed in terms of the number of islets present in the culture dish, or as a function of the measured total DNA content. The data obtained indicate that elimination of non-endocrine cells from cultured islets by specific mitotoxins does not impair islet function; in contrast, it may even enhance insulin release because the amount of insulin release into medium, when expressed in terms of DNA content, is significantly higher due to the homogeneity of the cell preparation obtained following treatment with the mitotoxin.

The combination of using BCEM, which is an excellent matrix to support the functioning of whole human islets in culture, and adding the basic FGF-saporin conjugates to these primary cell cultures has been found to offer a novel approach towards the establishment of islet cell monolayers for clinical and laboratory research.

Although the invention has been described with reference to the presently-preferred embodiments, it should be understood that various changes and modifications can be made without departing from the spirit of the invention, which is defined only by the claims appended hereto.

Particular features of the invention are set forth in the claims that follow.

What is claimed is:

1. A method for maintaining mammalian pancreatic islet cells in culture, which method comprises adding to the culture medium an effective amount of FGF conjugated to a cytotoxic agent.

2. The method of claim 1 wherein said conjugate is formed from mammalian basic FGF.

3. The method of claim 2 wherein said cytotoxic agent is a ribosome-inactivating protein.

4. The method of claim 3 wherein said cytotoxic agent is saporin.

5. The method of claim 1 wherein said islets are human pancreatic islets.

6. The method of claim 5 wherein said islets are grown in said culture on an extracellular matrix.

7. The method of claim 6 wherein said extracellular matrix is a bovine corneal endothelial cell matrix.

8. The method of claim 7 wherein an effective amount of glucose is also added to said cell culture medium to promote viability of said islet cells.

9. The method of claim 7 wherein an effective amount of insulin is also added to said cell culture medium to promote viability of said islet cells.

10. The method of claim 7 wherein an effective amount of recombinant human insulin is also added to said cell culture medium to promote viability of said islet cells.

11. The method of claim 7 wherein said conjugate is formed from basic FGF.

12. The method of claim 11 wherein said cytotoxic agent is a ribosome-inactivating protein.

13. The method of claim 11 wherein said cytotoxic agent is saporin and said basic FGF-saporin conjugate is daily added to said cell culture at a concentration of at least about 100 pM.

* * * * *